(12) United States Patent
Barranco et al.

(10) Patent No.: US 11,260,088 B2
(45) Date of Patent: Mar. 1, 2022

(54) METHODS FOR INCREASING GROWTH OF BENEFICIAL BACTERIA IN THE GASTROINTESTINAL TRACT

(71) Applicant: ABBOTT LABORATORIES, Abbott Park, IL (US)

(72) Inventors: Alejandro Perez Barranco, Las Gabias (ES); Maria Gonzalez Ramirez, Granada (ES); Rachael Buck, Gahanna, OH (US); Enrique Hernandez Vazquez, Ogijares (ES)

(73) Assignee: ABBOTT LABORATORIES, Abbott Park, IL (US)

( * ) Notice: Subject to any disclaimer, the term of this patent is extended or adjusted under 35 U.S.C. 154(b) by 17 days.

(21) Appl. No.: 16/625,429

(22) PCT Filed: Jun. 21, 2018

(86) PCT No.: PCT/US2018/038761
§ 371 (c)(1),
(2) Date: Dec. 20, 2019

(87) PCT Pub. No.: WO2018/237149
PCT Pub. Date: Dec. 27, 2018

(65) Prior Publication Data
US 2021/0113630 A1    Apr. 22, 2021

(30) Foreign Application Priority Data
Jun. 21, 2017   (EP) .................................... 17382381

(51) Int. Cl.
*A61K 31/702*   (2006.01)
*A61K 35/747*   (2015.01)
(Continued)

(52) U.S. Cl.
CPC .......... *A61K 35/747* (2013.01); *A23L 33/125* (2016.08); *A23L 33/135* (2016.08);
(Continued)

(58) Field of Classification Search
CPC ..................................................... A61K 31/702
See application file for complete search history.

(56) References Cited

U.S. PATENT DOCUMENTS 8,703,737 B2    4/2014   Buck et al.
8,802,650 B2    8/2014   Buck et al.
(Continued)

FOREIGN PATENT DOCUMENTS

| CA | 2831341 A1 | 10/2012 |
| WO | 2012092159 A1 | 7/2012 |
| WO | 2016086151 A1 | 6/2016 |

OTHER PUBLICATIONS

International Preliminary Patentability Report from PCT/US2018/038761 dated Dec. 24, 2019.
(Continued)

*Primary Examiner* — Rosanne Kosson
(74) *Attorney, Agent, or Firm* — Calfee Halter & Griswold LLP

(57) ABSTRACT

Disclosed are nutritional compositions including 2'-fucosyllactose (2'-FL) in combination with lutein and RRR-alpha-tocopherol. The nutritional compositions are useful for improving at least one of gut function, health, and development in an individual. In certain embodiments, the nutritional compositions can improve growth or maturation of the gut, as well as promote a healthy balance of beneficial bacteria in the gastrointestinal tract thereby treating and/or preventing formula intolerance or other gastrointestinal diseases and/or disorders resulting from suboptimal gastrointestinal flora population/balance.

17 Claims, 4 Drawing Sheets

(51) Int. Cl.
| | |
|---|---|
| A23L 33/125 | (2016.01) |
| A23L 33/15 | (2016.01) |
| A23L 33/135 | (2016.01) |
| A23L 33/00 | (2016.01) |
| A61P 1/14 | (2006.01) |
| A61K 9/107 | (2006.01) |
| A61K 31/015 | (2006.01) |
| A61K 31/047 | (2006.01) |
| A61K 31/07 | (2006.01) |
| A61K 31/122 | (2006.01) |
| A61K 31/14 | (2006.01) |
| A61K 31/145 | (2006.01) |
| A61K 31/205 | (2006.01) |
| A61K 31/355 | (2006.01) |
| A61K 31/405 | (2006.01) |
| A61K 31/4188 | (2006.01) |
| A61K 31/4415 | (2006.01) |
| A61K 31/519 | (2006.01) |
| A61K 31/525 | (2006.01) |
| A61K 31/593 | (2006.01) |
| A61K 31/7072 | (2006.01) |
| A61K 31/7076 | (2006.01) |
| A61K 31/708 | (2006.01) |
| A61K 31/714 | (2006.01) |
| A61K 33/06 | (2006.01) |
| A61K 33/26 | (2006.01) |
| A61K 33/30 | (2006.01) |
| A61K 35/20 | (2006.01) |
| A61K 35/745 | (2015.01) |
| A61K 47/02 | (2006.01) |
| A61K 47/12 | (2006.01) |
| A61K 47/14 | (2017.01) |
| A61K 47/22 | (2006.01) |
| A61K 47/24 | (2006.01) |
| A61K 47/26 | (2006.01) |
| A61K 47/36 | (2006.01) |
| A61K 47/42 | (2017.01) |
| A61K 47/44 | (2017.01) |
| A61K 47/46 | (2006.01) |

(52) U.S. Cl.
CPC ............... *A23L 33/15* (2016.08); *A23L 33/40* (2016.08); *A61K 9/107* (2013.01); *A61K 31/015* (2013.01); *A61K 31/047* (2013.01); *A61K 31/07* (2013.01); *A61K 31/122* (2013.01); *A61K 31/14* (2013.01); *A61K 31/145* (2013.01); *A61K 31/205* (2013.01); *A61K 31/355* (2013.01); *A61K 31/405* (2013.01); *A61K 31/4188* (2013.01); *A61K 31/4415* (2013.01); *A61K 31/519* (2013.01); *A61K 31/525* (2013.01); *A61K 31/593* (2013.01); *A61K 31/702* (2013.01); *A61K 31/708* (2013.01); *A61K 31/7072* (2013.01); *A61K 31/7076* (2013.01); *A61K 31/714* (2013.01); *A61K 33/06* (2013.01); *A61K 33/26* (2013.01); *A61K 33/30* (2013.01); *A61K 35/20* (2013.01); *A61K 35/745* (2013.01); *A61K 47/02* (2013.01); *A61K 47/12* (2013.01); *A61K 47/14* (2013.01); *A61K 47/22* (2013.01); *A61K 47/24* (2013.01); *A61K 47/26* (2013.01); *A61K 47/36* (2013.01); *A61K 47/42* (2013.01); *A61K 47/44* (2013.01); *A61K 47/46* (2013.01); *A61P 1/14* (2018.01); *A23V 2002/00* (2013.01)

(56) References Cited

U.S. PATENT DOCUMENTS

| | | |
|---|---|---|
| 9,049,883 B2 | 6/2015 | Koenig et al. |
| 9,192,179 B2 | 11/2015 | Roughead et al. |
| 9,492,473 B2 | 11/2016 | von Maltzahn et al. |
| 9,539,269 B2 | 1/2017 | Chow et al. |
| 2012/0172319 A1 | 7/2012 | Chow et al. |
| 2012/0208782 A1 | 8/2012 | Frantz |
| 2012/0294840 A1 | 11/2012 | Newburg et al. |
| 2014/0037603 A1 | 2/2014 | Bolster et al. |
| 2014/0056862 A1 | 2/2014 | Greenberg et al. |
| 2014/0056863 A1 | 2/2014 | Greenberg et al. |
| 2014/0249103 A1 | 9/2014 | Buck et al. |
| 2014/0294788 A1 | 10/2014 | Bailey et al. |
| 2014/0356340 A1 | 12/2014 | Burbidge et al. |
| 2014/0357576 A1 | 12/2014 | Breuille et al. |
| 2016/0100617 A1 | 4/2016 | Roughead et al. |

OTHER PUBLICATIONS

International Search Report from PCT/US2018/038761 dated Sep. 25, 2018.
Office Action from Vietnamese Application No. 1-2019-07481 dated Feb. 19, 2020.
Angeliki et al., "Breast Milk Tocopherol Content During The First Six Months In Exclusively Breastfeeding Greek Women," European Journal Of Nutrition, vol. 50, No. 3, Aug. 19, 2010, pp. 195-202.
Gomez-Gallego et al., The human milk microbiome and factors influencing its composition and activity, Seminars In Fetal and Neonatal Medicine, vol. 21, No. 6, May 31, 2017, pp. 400-405.
Good, et al., "The Human Milk Oligosaccharide 2'-Fucosyllactose Attenuates the Severity of Experimental Necrotising Enterocolitis by Enhancing Mesenteric Perfusion in the Neonatal Intestine" Br J Nutr. Oct. 2016: 116(7): pp. 1175-1187.
Jewell et al., A Comparison of Lutein and Zeaxanthin Concentralions In Formula and Human Milk Samples From Northern Ireland Mothers, European Journal of Clinical Nutrit, vol. 58, No. 1, Jan. 1, 2004, pp. 90-97.
Pia et al., "Association Between Breast Milk Bacterial Communities and Establishment and Devleeopment of the Infant Gut Microbiome," JAMA Pediatrics, vol. 171, No. 7, May 8, 2017, p. 647.
Shashank et al. "Supplementation with RRR- or All-rac-[alpha]-Tocopherol Differentially Affects the [alpha]-Tocopherol Stereoisomer Profile in the Mlik and Plasma of Lactating Women," The Journal of Nutrition, vol. 147, No. 7, May 31, 2017 pp. 1301-1307.
Communication Pursuant to Article 94(3) EPC from European Application No. 18735485.7 dated Oct. 26, 2020.
Office Action from Russian Application No. 2020100133 dated Jun. 17, 2020.
Communication Pursuant to Article 94(3) EPC from European Application No. 18735485.7 dated Mar. 12, 2021.
Written Opinion from Singapore Application No. 11201912551U dated Jul. 5, 2021.
McGuire M. K. et al., What's normal? Oligosaccharide concentrations and profiles in milk produced by healthy women vary geographically. Am J Clin Nutr, Mar. 29, 2017, vol. 105, No. 5, pp. 1086-1100.

METHODS FOR INCREASING GROWTH OF BENEFICIAL BACTERIA IN THE GASTROINTESTINAL TRACT

CROSS REFERENCE TO RELATED APPLICATIONS

This application is the U.S. national stage entry of International Application No. PCT/US2018/038761, filed Jun. 21, 2018, which claims priority to and the benefit of European Patent Application No. 17382381.6, filed on Jun. 21, 2017, the entire contents of which are incorporated herein by reference.

FIELD

The present disclosure generally relates to compositions and methods for improving at least one of gut function, health, and development in an infant, toddler, child, or adult, along with related methods of treatment, prevention, as well as non-therapeutic use. More particularly, the present disclosure relates to nutritional compositions comprising 2'-fucosyllactose, lutein, and RRR-alpha-tocopherol and the associated methods of use.

BACKGROUND

During postnatal development, a newborn's intestine experiences a process of maturation that ends with the production of gastrointestinal epithelium that functions as a selective barrier (i.e., gut barrier). The gastrointestinal epithelium permits the absorption of nutrients, electrolytes and water, while preventing exposure to dietary and microbial antigens, including food allergens. Specifically, this barrier limits the passage of antigens to the systemic circulation, thereby preventing infection, inflammatory reactions, and other gastrointestinal diseases and disorders that may occur during infancy and later in life. For very young infants, and particularly, preterm infants, who have an immature immune system and intestinal tract, development of suboptimal intestinal flora can hinder development and may result in infection, diarrhea, allergies, and food intolerance.

Breastfeeding has been associated with enhanced development and balanced growth and maturation of the infant's biological systems, including the gastrointestinal system, thereby providing protection of the infant to infection and other gut-related conditions and diseases. Among other components, breast milk includes human milk oligosaccharides that not only act as pathogen receptor analogues, but activate immune factors by infant intestinal epithelial cells and/or associated immune cell populations.

However, not all infants are in a position to receive human breast milk and the benefits associated with it. Likewise, human breast milk may not be suitable for others such as toddlers, children, and adults, thereby excluding many from the benefits of human breast milk.

SUMMARY

The nutritional compositions according to the general inventive concepts can produce nutritional benefits including improved gastrointestinal growth, development, and maturation. In addition, the nutritional compositions can enhance immunity against microbial infections and other gastrointestinal diseases, conditions, and disorders.

The present disclosure is directed to nutritional compositions, including synthetic infant formulas, synthetic pediatric formulas, synthetic child formulas, and synthetic adult formulas including 2'-fucosyllactose (2'-FL) in combination with lutein and RRR-alpha-tocopherol for improving at least one of gut function, health, and development in an infant, toddler, child, or adult, along with related methods of treatment, prevention, and non-therapy use. In exemplary embodiments, the nutritional compositions can improve growth or maturation of the gut, as well as promote a healthy balance of beneficial bacteria in the gastrointestinal tract (e.g., treat gut dysbiosis) thereby treating and/or preventing formula intolerance (i.e., fussiness, gas, crying, colic) or other gastrointestinal diseases and/or disorders resulting from suboptimal gastrointestinal flora population/balance (e.g., antibiotic induced dysbiosis).

An exemplary embodiment is directed to a method of improving the gut health of an infant, toddler, child or adult. The method comprises administering to the infant, toddler, child, or adult a composition comprising 2'-fucosyllactose, lutein, and RRR-alpha-tocopherol. In certain exemplary embodiments, the infant, toddler, child, or adult is in need of improved gut health.

An exemplary embodiment is directed to a composition for improving the gut health of an infant, toddler, child or adult. The composition comprises 2'-fucosyllactose, lutein, and RRR-alpha-tocopherol. More particularly, the composition comprises from about 0.02 mg/mL to about 20 mg/mL of 2'-fucosyllactose, from about 0.001 mg/mL to about 5 mg/mL of lutein, and from about 3 mg/L to about 100 mg/L of RRR-alpha-tocopherol.

An exemplary embodiment is directed to a method of increasing the beneficial bacteria in the gastrointestinal tract of an infant, toddler, child, or adult. The method comprises administering to the infant, toddler, child, or adult a composition comprising 2'-fucosyllactose, lutein, and RRR-alpha-tocopherol. In certain exemplary embodiments, the infant, toddler, child, or adult is in need of increased beneficial bacteria in the gastrointestinal tract.

An exemplary embodiment is directed to a composition for increasing the beneficial bacteria in the gastrointestinal tract of an infant, toddler, child, or adult. The composition comprises 2'-fucosyllactose, lutein, and RRR-alpha-tocopherol. More particularly, the composition comprises from about 0.02 mg/mL to about 20 mg/mL of 2'-fucosyllactose, from about 0.001 mg/mL to about 5 mg/mL of lutein, and from about 3 mg/L to about 100 mg/L of RRR-alpha-tocopherol.

An exemplary embodiment is directed to a method of improving the feeding tolerance of an infant, toddler, child, or adult. The method comprises administering to the infant, toddler, child, or adult a composition comprising 2'-fucosyllactose, lutein, and RRR-alpha-tocopherol. In certain exemplary embodiments, the infant, toddler, child, or adult is in need of improved feeding tolerance.

An exemplary embodiment is directed to a composition for improving the feeding tolerance of an infant, toddler, child, or adult. The composition comprises 2'-fucosyllactose, lutein, and RRR-alpha-tocopherol. More particularly, the composition comprises from about 0.02 mg/mL to about 20 mg/mL of 2'-fucosyllactose, from about 0.001 mg/mL to about 5 mg/mL of lutein, and from about 3 mg/L to about 100 mg/L of RRR-alpha-tocopherol.

An exemplary embodiment is directed to a method of treating dysbiosis in an infant, toddler, child, or adult. The method comprises administering to the infant, toddler, child, or adult a composition comprising 2'-fucosyllactose, lutein, and RRR-alpha-tocopherol.

An exemplary embodiment is directed to a composition for treating dysbiosis in an infant, toddler, child, or adult. The composition comprises 2'-fucosyllactose, lutein, and RRR-alpha-tocopherol. More particularly, the composition comprises from about 0.02 mg/mL to about 20 mg/mL of 2'-fucosyllactose, from about 0.001 mg/mL to about 5 mg/mL of lutein, and from about 3 mg/L to about 100 mg/L of RRR-alpha-tocopherol.

An exemplary embodiment is directed to the use of a nutritional composition comprising 2'-fucosyllactose, lutein, and RRR-alpha-tocopherol for improving gut health of an infant.

An exemplary embodiment is directed to the use of a nutritional composition comprising 2'-fucosyllactose, lutein, and RRR-alpha-tocopherol for treating at least one of dysbiosis and feeding intolerance.

An exemplary embodiment is directed to the use of a nutritional composition comprising 2'-fucosyllactose, lutein, and RRR-alpha-tocopherol for increasing the beneficial bacteria in the gastrointestinal tract of an infant.

Moreover, it has been found that gut health of an infant, toddler, child, or adult can be significantly improved by administering to the infant, toddler, child, or adult a synbiotic composition including the 2'-FL, lutein, and RRR-alpha-tocopherol of the present disclosure. Specifically, the synbiotic combination includes a probiotic, 2'-FL, lutein, and RRR-alpha-tocopherol. The synbiotic composition promotes the colonization of beneficial intestinal microbiota in order to discourage the growth of harmful bacteria, thereby balancing the microflora in the gastrointestinal tract. As such the gut function may be improved and gastrointestinal issues are reduced or minimized.

Although the nutritional compositions and methods may primarily be discussed herein in relation to preterm infants and infants in general, it should be understood that many of the benefits discussed herein may be provided to toddlers, children, and adults administered 2'-FL, lutein, and RRR-alpha-tocopherol, or with other components as described herein, such as prebiotic oligosaccharides and/or probiotics, for example. Particularly, in some embodiments, the incidence of gastrointestinal diseases and disorders that generally affect adults, such as Crohn's disease, ulcerative colitis, irritable bowel syndrome and the like, can be reduced with the use of the nutritional compositions according to the general inventive concepts.

DETAILED DESCRIPTION

Figure 1:
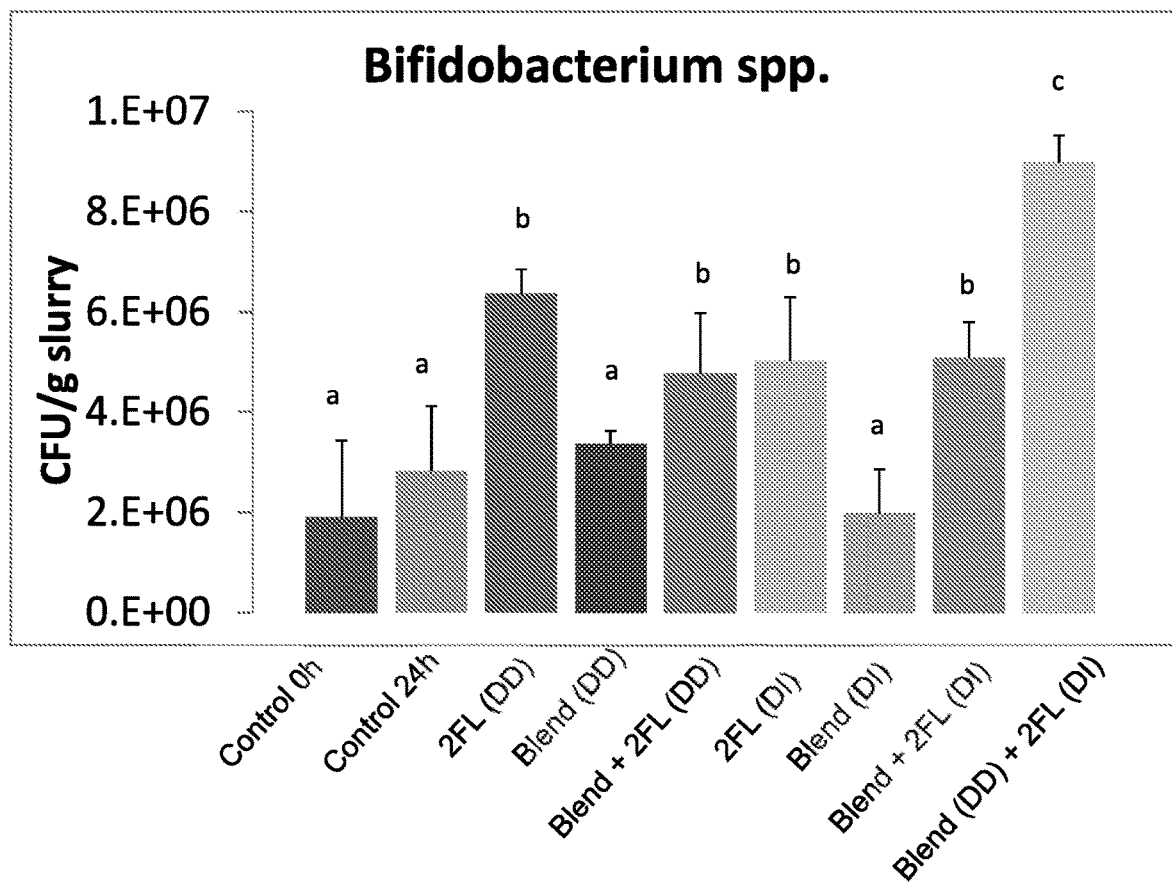
FIG. 1 is a graph showing the concentration of Bifidobacteria in fecal samples after exposure to a variety of mixtures, measured by real time-PCR. Bars with different letters are significantly different at $p<0.05$.

Several illustrative embodiments will be described in detail with the understanding that the present disclosure merely exemplifies the general inventive concepts. Embodiments encompassing the general inventive concepts may take various forms and the general inventive concepts are not intended to be limited to the specific embodiments described herein.

The nutritional compositions and methods described herein utilize the Human Milk Oligosaccharide (HMO) 2'-fucosyllactose in combination with lutein and RRR-alpha-tocopherol for controlling, treating, and reducing a number of diseases, disorders and conditions related to the gastrointestinal tract, especially those related to gut maturation and an improved microbiome profile/balance in the gastrointestinal tract. These and other features of the nutritional compositions and methods, as well as some of the many optional variations and additions, are described in detail hereafter.

More particularly, the general inventive concepts are directed to nutritional compositions including 2'-fucosyllactose (2'-FL) in combination with lutein and RRR-alpha-tocopherol for improving at least one of gut function, health, and development in an infant, toddler, child, or adult, along with related methods of treatment, prevention, and non-therapy use. The nutritional compositions can improve growth and maturation of the gut, as well as promote a healthy balance of beneficial bacteria in the gastrointestinal tract (e.g., treat gut dysbiosis) thereby treating and/or preventing formula intolerance or other gastrointestinal diseases and/or disorders resulting from suboptimal gastrointestinal flora population/balance.

Administration of the nutritional compositions for improving gut maturation and gut health early in life may also reduce the risk of developing associated conditions and diseases of the gastrointestinal tract later in life. Diseases known to be associated with suboptimal gut maturation and/or gut dysbiosis include, but are not limited to, irritable bowel syndrome, colitis (e.g., necrotizing enterocolitis, Crohn's disease, ischemic colitis, *cryptosporidium* enterocolitis, pseudomembranous colitis, cytomegalovirus, ulcerative colitis), inflammatory bowel disease, celiac disease, colic, food intolerance, and food allergies. Thus, in certain exemplary embodiments, the general inventive concepts also contemplate nutritional compositions including 2'-fucosyllactose in combination with lutein and RRR-alpha-tocopherol for treating and/or reducing the risk of irritable bowel syndrome, colitis (e.g., necrotizing enterocolitis, Crohn's disease, ischemic colitis, *cryptosporidium* enterocolitis, pseudomembranous colitis, cytomegalovirus, ulcerative colitis), inflammatory bowel disease, celiac disease, obesity, metabolic syndrome, food intolerance, food allergies, colic, *C. difficile* infection and antibiotic-induced dysbiosis.

It has surprisingly been found that the combination of 2'-fucosyllactose in combination with lutein and RRR-alpha-tocopherol can synergistically promote the growth of two strains of beneficial bacteria, namely, Bifidobacteria and Lactobacilli. In this regard, the nutritional compositions can improve the gut health of either the large intestine, the small intestine, or both. In certain exemplary embodiments, nutritional compositions including 2'-fucosyllactose in combination with lutein and RRR-alpha-tocopherol synergistically promote the growth of Bifidobacteria, which resides in the large intestine. In certain exemplary embodiments, nutritional compositions including 2'-fucosyllactose in combination with lutein and RRR-alpha-tocopherol synergistically promote the growth of Lactobacilli, which reside in the small intestine.

Definitions

The terms "fat" and "oil" as used herein, unless otherwise specified, are used interchangeably to refer to lipid materials derived or processed from plants or animals. These terms also include synthetic lipid materials so long as such synthetic materials are suitable for oral administration to humans.

The term "human milk oligosaccharide" or "HMO", unless otherwise specified, refers generally to a number of complex carbohydrates found in human breast milk that can be in acidic or neutral form, and to precursors thereof. One HMO of particular interest is 2'-fucosyllactose.

The terms "nutritional formulation" or "nutritional composition" as used herein, are used interchangeably and, unless otherwise specified, refer to synthetic formulas including nutritional liquids, nutritional powders, nutritional solids, nutritional semi-solids, nutritional semi-liquids, nutritional supplements, and any other nutritional food product as known in the art. The nutritional powders may be reconstituted to form a nutritional liquid, all of which comprise one or more of fat, protein and carbohydrate and are suitable for oral consumption by a human. The terms "nutritional formulation" or "nutritional composition" do not include human breast milk whether in natural or supplemented form.

The term "nutritional liquid" as used herein, unless otherwise specified, refers to nutritional compositions in ready-to-drink liquid form, concentrated form, and nutritional liquids made by reconstituting the nutritional powders described herein prior to use.

The term "nutritional powder" as used herein, unless otherwise specified, refers to nutritional compositions in flowable or scoopable form that can be reconstituted with water or another aqueous liquid prior to consumption and includes both spray-dried and drymixed/dryblended powders.

The term "nutritional semi-solid," as used herein, unless otherwise specified, refers to nutritional products that are intermediate in properties, such as rigidity, between solids and liquids. Some semi-solids examples include puddings, gelatins, and doughs.

The term "nutritional semi-liquid," as used herein, unless otherwise specified, refers to nutritional products that are intermediate in properties, such as flow properties, between liquids and solids. Some semi-liquids examples include thick shakes and liquid gels.

The term "individual" as used herein, refers generally to a person, whether an infant, toddler, child, or adult. In certain embodiments, the individual is susceptible to, or at risk of, one or more of the conditions or diseases discussed herein. In certain embodiments, the individual is a healthy individual.

The term "infant" as used herein, refers generally to individuals up to age 36 months of age, actual or corrected and in certain instances may include toddlers. In certain embodiments, the term infant refers to individuals up to 12 months of age. The term "preterm infant" as used herein refers to those infants born at less than 37 weeks gestation, have a birth weight of less than 2500 gm, or both. The term "toddler" as used herein, unless otherwise specified, refers to a person greater than one year of age up to three years of age.

The term "child" as used herein, unless otherwise specified, refers to a person greater than three years of age up to twelve years of age.

The terms "infant formula" or "synthetic infant formula" as used herein, unless otherwise specified, are used interchangeably and refer to liquid, semiliquid, solid, and semi-solid human milk replacements or substitutes that are suitable for consumption by an infant.

The term "synthetic child formula" as used herein, unless otherwise specified, refers to liquid, semi-liquid, solid, and semi-solid human milk replacements or substitutes that are suitable for consumption by a child up to the age of 12 years. The term "synthetic child nutritional formula" does not include human breast milk.

The term "preterm infant formula" as used herein, unless otherwise specified, refers to liquid and solid nutritional products suitable for consumption by a preterm infant.

The term "human milk fortifier" as used herein, unless otherwise specified, refers to liquid and solid nutritional products suitable for mixing with breast milk or preterm infant formula or infant formula for consumption by a preterm or term infant.

The terms "susceptible" and "at risk" as used herein, unless otherwise specified, mean having little resistance to a certain condition or disease, including being genetically predisposed, having a family history of, and/or having symptoms of the condition or disease, especially those who are at elevated risk as compared to the general population.

All percentages, parts and ratios as used herein, are by weight of the total composition, unless otherwise specified. All such weights, as they pertain to listed ingredients, are based on the active level and, therefore, do not include solvents or by-products that may be included in commercially available materials, unless otherwise specified.

Ranges as used herein are intended to include every number and subset of numbers within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The nutritional compositions and methods may comprise, consist of, or consist essentially of the essential elements of the compositions and methods as described herein, as well as any additional or optional element described herein or otherwise useful in nutritional composition applications.

The nutritional compositions of the present disclosure may also be substantially free of any optional or selected essential ingredient or feature described herein, provided that the remaining composition or formula still contains all of the required ingredients or features as described herein. In this context, and unless otherwise specified, the term "substantially free" means that the selected composition contains less than a functional amount of the optional ingredient, typically less than 0.1% by weight, and also including zero percent by weight of such optional or selected essential ingredient.

Product Form

The nutritional compositions of the present disclosure may be formulated and administered in any known or otherwise suitable oral product form. Any solid, semi-solid, liquid, semi-liquid, or powder product form, including combinations or variations thereof, are suitable for use herein, provided that such forms allow for safe and effective oral delivery to the individual of the essential ingredients and any optional ingredients, as also defined herein.

The nutritional composition may be formulated with sufficient kinds and amounts of nutrients to provide a sole, primary, or supplemental source of nutrition, or to provide a specialized nutritional composition for use in individuals afflicted with specific diseases, disorders, or conditions or with a targeted nutritional benefit as described below.

Nutritional Liquids

Nutritional liquids include both concentrated and ready-to-feed nutritional liquids. These nutritional liquids are most typically formulated as suspensions or emulsions, although other liquid forms are within the scope of the present disclosure.

In exemplary embodiments, nutritional liquids suitable for use may be aqueous emulsions comprising proteins, fats, and carbohydrates. These emulsions are generally flowable or drinkable liquids at from about 1° C. to about 25° C. and are typically in the form of oil-in-water, water-in-oil, or complex aqueous emulsions, although such emulsions are most typically in the form of oil-in-water emulsions having a continuous aqueous phase and a discontinuous oil phase.

The nutritional liquids may have a caloric density tailored to the nutritional needs of the ultimate user, although in most instances the liquids comprise generally at least 19 kcal/fl oz (660 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-24 kcal/fl oz nutritional liquids are more commonly used in preterm or low birth weight infants, and the 20-21 kcal/fl oz (675-680 to 700 kcal/liter) nutritional liquids are more often used in term infants. In some embodiments, the nutritional liquids may have a caloric density of from about 50-100 kcal/liter to about 660 kcal/liter, including from about 150 kcal/liter to about 500 kcal/liter. In some specific embodiments, the nutritional liquids may have a caloric density of 25, or 50, or 75, or 100 kcal/liter.

Although the serving size for the nutritional liquid can vary depending upon a number of variables, a typical serving size is generally at least about 1 mL, or even at least about 2 mL, or even at least about 5 mL, or even at least about 10 mL, or even at least about 25 mL, including ranges from about 2 mL to about 300 mL, including from about 4 mL to about 250 mL, and including from about 10 mL to about 240 mL.

Nutritional Solids

The nutritional solids may be in any solid form, but are typically in the form of flowable or substantially flowable particulate compositions, or at least particulate compositions. Particularly suitable nutritional solid product forms include spray dried, agglomerated and/or dryblended powder compositions. The compositions can easily be scooped and measured with a spoon or similar other device, and can easily be reconstituted by the intended user with a suitable aqueous liquid, typically water, to form a nutritional composition for immediate oral or enteral use. In this context, "immediate" use generally means within about 48 hours, most typically within about 24 hours, preferably right after reconstitution.

The nutritional powders may be reconstituted with water prior to use to a caloric density tailored to the nutritional needs of the ultimate user, although in most instances the powders are reconstituted with water to form compositions comprising at least 19 kcal/fl oz (660 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-24 kcal/fl oz reconstituted powders are more commonly used in preterm or low birth weight infants, and the 20-21 kcal/fl oz (675-680 to 700 kcal/liter) reconstituted powders are more often used in term infants. In some embodiments, the reconstituted powder may have a caloric density of from about 50-100 kcal/liter to about 660 kcal/liter, including from about 150 kcal/liter to about 500 kcal/liter. In some specific embodiments, the reconstituted powders may have a caloric density of 25, or 50, or 75, or 100 kcal/liter.

Human Milk Oligosaccharides (HMOs)

The nutritional compositions of the present disclosure include 2'-fucosyllactose (2'-FL) and optionally, one or more additional HMOs. The compositional structure of HMOs is very complex and more than 200 different oligosaccharide-like structures are known.

In accordance with the present disclosure, the 2'-fucosyllactose is included in the nutritional compositions in combination with lutein, RRR-alpha-tocopherol, and optionally other components (probiotics, etc.) as described herein. The 2'-fucosyllactose or optional HMOs may be isolated or enriched from milk(s) secreted by mammals including, but not limited to: human, bovine, ovine, porcine, or caprine species. The 2'-fucosyllactose or optional HMOs may also be produced via microbial fermentation, enzymatic processes, chemical synthesis, or combinations thereof.

The nutritional compositions described herein include a nutritionally significant quantity of 2'-fucosyllactose. The amount of 2'-fucosyllactose present in the nutritional compositions can vary depending on the individual, the intended use, or both. In certain exemplary embodiments, the 2'-fucosyllactose is present in the infant formula at a concentration effective to treat one or more of gut function, gut health, gut development, gut flora imbalance (dysbiosis), feeding intolerance, and any other methods in accordance with the present disclosure. In certain exemplary embodiments, 2'-fucosyllactose is present in an amount of at least 0.02 mg/mL of the nutritional composition. In certain exemplary embodiments, 2'-fucosyllactose is present in a concentration from about 0.02 mg/mL to about 20 mg/mL, including from about 0.02 mg/mL to about 10 mg/mL, including from about 0.05 mg/mL to about 5 mg/mL, including from about 0.2 mg/mL to about 2 mg/mL, including from about 0.2 mg/mL to about 1 mg/mL, including from about 0.5 mg/mL to about 1 mg/mL. In certain exemplary embodiments, 2'-fucosyllactose is present in a concentration of about 0.02 mg/mL, about 0.025 mg/mL, about 0.05 mg/mL, about 0.075 mg/mL, about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1.0 mg/mL, about 1.2 mg/mL, about 1.4 mg/mL, about 1.6 mg/mL, about 1.8 mg/mL, about 2.0 mg/mL, about 5.0 mg/mL, about 7.5 mg/mL, about 10 mg/mL, about 15 mg/mL, or about 20 mg/mL.

In addition to the 2'-fucosyllactose described above, in certain exemplary embodiments the nutritional composition optionally includes additional sialylated, fucosylated, or n-acetylglucosylated human milk oligosaccharides (HMOs).

Specific non-limiting examples of additional HMOs or HMO-precursors that may be included individually or in combination in the compositions of the present disclosure include: sialic acid (i.e., free sialic acid, lipid-bound sialic acid, protein-bound sialic acid); D-glucose (Glc); D-galactose (Gal); N-acetylglucosamine (GlcNAc); L-fucose (Fuc); fucosyl oligosaccharides (i.e., Lacto-N-fucopentaose I; Lacto-N-fucopentaose II; 3'-Fucosyllactose; Lacto-N-fucopentaose III; Lacto-N-difucohexaose I; and Lactodifucotetraose); non-fucosylated, non-sialylated oligosaccharides (i.e., Lacto-N-tetraose and Lacto-N-neotetraose); sialyl oligosaccharides (i.e., 3'-Sialyl-3-fucosyllactose; Disialomonofucosyllacto-N-neohexaose; Monofucosylmonosialyllacto-N-octaose (sialyl Lea); Sialyllacto-N-fucohexaose II; Disialyllacto-N-fucopentaose II; Monofucosyldisialyllacto-N-tetraose); and sialyl fucosyl oligosaccharides (i.e., 2'-Sialyllactose; 2-Sialyllactosamine; 3'-Sialyllactose; 3'-Sialyllactosamine; 6'-Sialyllactose; 6'-Sialyllactosamine; Sialyllacto-N-neotetraose c; Monosialyllacto-N-hexaose; Disialyllacto-N-hexaose I; Monosialyllacto-N-neohexaose I; Monosialyllacto-N-neohexaose II; Disialyllacto-N-neohexaose; Disialyllacto-N-tetraose; Disialyllacto-N-hexaose II; Sialyllacto-N-tetraose a; Disialyllacto-N-hexaose I; and Sialyllacto-N-tetraose b). Also useful are variants in which the glucose (Glc) at the reducing end is replaced by N-acetylglucosamine (e.g., 2'-fucosyl-N-acetylglucosamine (2'-FLNac) is such a variant to 2'-fucosyllactose).

The optional HMOs may be present in the nutritional compositions in total amounts of HMO in the composition of at least about 0.02 mg/mL, including from about 0.02 mg/mL to about 20 mg/mL, including from about 0.02 mg/mL to about 20 mg/mL, including from about 0.02 mg/mL to about 15 mg/mL, including from about 0.02 mg/mL to about 15 mg/mL, including from about 0.02 mg/mL to about 10 mg/mL, including from about 0.02 mg/mL to about 10 mg/mL, including from about 0.02 mg/mL to about 5 mg/mL, including from about 0.02 mg/mL to about 5 mg/mL, and including from about 0.02 mg/mL to about 1 mg/mL of total HMO in the nutritional composition. Typically, the amount of HMO in the nutritional composition will depend on the specific HMO or HMOs present and the amounts of other components in the nutritional compositions.

Carotenoids

The nutritional compositions described herein include a nutritionally significant quantity of lutein. Lutein has been shown to provide oxidative protection, as well as to enhance brain development. The lutein present in the inventive nutritional compositions may be provided as a part of a mixture of carotenoids or by itself. As used herein, the term "lutein" is intended to refer to all isomers of the compound.

The amount of lutein present in the nutritional compositions can vary depending on the individual, the intended use, or both. In certain exemplary embodiments, the lutein is present in the infant formula at a concentration effective to improve one or more of gut health, gut function, gut development, gut flora balance (dysbiosis), feeding tolerance and any other methods in accordance with the present disclosure. In certain exemplary embodiments, lutein is present in a concentration of at least about 0.001 mg/mL, including from about 0.001 mg/mL to 5 mg/mL, including from about 0.001 mg/mL to about 2 mg/mL, including from about 0.001 mg/mL to about 1 mg/mL, including from about 0.001 mg/mL to about 0.044 mg/mL, including from about 0.001 mg/mL to about 0.0190 mg/mL, including from about 0.001 mg/mL to about 0.0140 mg/mL, including from about 0.01 mg/mL to about 5 mg/mL, including from about 0.01 mg/mL to about 2 mg/mL, including from about 0.01 mg/mL to about 1 mg/mL, including from about 0.01 mg/mL to about 0.044 mg/mL, including from about 0.01 mg/mL to about 0.0190 mg/mL, including from about 0.01 mg/mL to about 0.0140 mg/mL, including about 0.044 mg/mL to about 5 mg/mL, including from about 0.044 mg/mL to about 2 mg/mL, including from about 0.044 mg/mL to about 1 mg/mL, including from about 0.044 mg/mL to about 0.1 mg/mL, including from about 0.1 mg/mL to about 5 mg/mL, including from about 0.1 mg/mL to about 2 mg/mL, including from about 0.1 mg/mL to about 1 mg/mL of lutein.

In certain exemplary embodiments, the nutritional compositions include one or more additional carotenoids such as beta-carotene, zeaxanthin, lycopene, and combinations thereof. It should be understood that any combination of beta-carotene, zeaxanthin, and lycopene can be included along with lutein in the nutritional compositions of the present disclosure.

RRR-Alpha-Tocopherol

The nutritional compositions described herein include a nutritionally significant quantity of RRR-alpha-tocopherol. Tocopherols can exist in a number of stereoisomeric forms depending on the chirality of the phytyl tail. Of the alpha-tocopherols, RRR-alpha-tocopherol (also referred to as "natural vitamin E") has the greatest biological activity and is reported to be the dominant form of alpha-tocopherol in the brain. RRR-alpha-tocopherol is a single stereoisomer whereas synthetic vitamin E (all-rac-alpha-tocopherol or tocopherol acetate) is an equimolar mixture of eight isomers, only one of which is RRR-alpha-tocopherol.

As used herein, the term "RRR-alpha-tocopherol" refers both to exogenous sources and inherent sources of RRR-alpha-tocopherol and RRR-alpha-tocopherol acetate that are present in a nutritional composition. Inherent sources include RRR-alpha-tocopherol that is inherently present in components that are present in a nutritional composition and may include for example, various oils and fats. Exogenous sources of RRR-alpha-tocopherol include RRR-alpha-tocopherol that is added to the infant formula not as part of another component.

The amount of RRR-alpha-tocopherol present in the nutritional compositions can vary depending on the individual, the intended use, or both. In certain exemplary embodiments, the RRR-alpha-tocopherol is present in the nutritional composition at a concentration effective to improve one or more of gut health, gut function, gut development, gut flora balance (dysbiosis), feeding tolerance, and any other methods in accordance with the present disclosure. In certain exemplary embodiments, RRR-alpha-tocopherol is present in the nutritional composition in a concentration of at least about 3 mg/L. In certain exemplary embodiments, RRR-alpha-tocopherol is present in a concentration of about 3 mg/L to about 100 mg/L, including from about 3 mg/L to about 50 mg/L, including from about 3 mg/L to about 40 mg/L, including from about 3 mg/L to about 35 mg/L, including from about 3 mg/L to about 25 mg/L, including from about 5 mg/L to about 100 mg/L, including from about 5 mg/L to about 50 mg/L, including from about 5 mg/L to about 40 mg/L, including from about 5 mg/L to about 35 mg/L, including from about 5 mg/L to about 25 mg/L including from about 7 mg/L to about 100 mg/L, including from about 7 mg/L to about 50 mg/L, including from about 7 mg/L to about 40 mg/L, including from about 7 mg/L to about 35 mg/L, including from about 7 mg/L to about 25 mg/L, including from about 10 mg/L to about 100 mg/L, including from about 10 mg/L to about 50 mg/L including from about 10 mg/L to about 40 mg/L, including from about 10 mg/L to about 35 mg/L, including from about 10 mg/L to about 25 mg/L, including from about 25 mg/L to about 100 mg/L, including from about 25 mg/L to about 50 mg/L, including from about 25 mg/L to about 40 mg/L, including from about 25 mg/L to about 35 mg/L of RRR-alpha-tocopherol.

Additional Oligosaccharides

The nutritional compositions of the present disclosure may, in addition to the 2'-FL and other HMOs described above, comprise an additional source or sources of prebiotic oligosaccharides (the total amount of oligosaccharides being referred to herein as an "oligosaccharide blend" of the nutritional composition). Suitable additional sources of prebiotic oligosaccharides for use in the nutritional compositions include any prebiotic oligosaccharide that is suitable for use in an oral nutritional composition and is compatible with the essential elements and features of such compositions.

Non-limiting examples of suitable additional prebiotic oligosaccharides for use in the nutritional compositions described herein include prebiotic oligosaccharides that have a degree of polymerization (DP) of at least 2 monose units, which are not or only partially digested in the intestine by the action of acids or digestive enzymes present in the human upper digestive tract (small intestine and stomach), but which are fermentable by the human intestinal flora. The term "monose units" refers to units having a closed ring structure, preferably hexose, e.g., the pyranose or furanose forms. Particularly preferred oligosaccharides for use in combination with the HMO or HMOs in the nutritional compositions of the present disclosure include galactooligosaccharides (GOS), fructooligosaccharides (FOS), short chain fructooligosaccharides, inulin, polydextrose (PDX), pectin hydrolysate, pectin acidic oligosaccharides, and gum fiber. In one specific embodiment, the gum fiber is gum arabic.

Probiotics

The nutritional compositions of the present disclosure may, in addition to 2'-fucosyllactose, lutein, and RRR-alpha-tocopherol, comprise one or more probiotic(s) from the *Lactobacillus* and/or the *Bifidobacterium* genera.

Non-limiting examples of probiotic strains for use in the nutritional compositions herein include the genus *Lactobacillus* including *L. acidophilus, L. amylovorus, L. brevis, L. bulgaricus, L. casei* spp. *casei, L. casei* spp. *rhamnosus, L. crispatus, L. delbrueckii* ssp. *lactis, L. fermentum, L. helveticus, L. johnsonii, L. paracasei, L. pentosus, L. plantarum, L. reuteri*, and L. sake; the genus *Bifidobacterium* including: *B. animalis, B. bifidum, B. breve, B. infantis*, and *B. longum*; the genus *Pediococcus* including: *P. acidilactici*; the genus *Propionibacterium* including: *P. acidipropionici, P. freudenreichii, P. jensenii*, and P. theonii; and the genus *Streptococcus* including: *S. cremoris, S. lactis*, and *S. thermophilus*. Particularly preferred probiotics include probiotics of human infant origin such as *B. infantis* M-63, *B. infantis* ATCC 15697, *B. infantis* 35624, *B. infantis* CHCC2228, *B. infantis* BB-02, *B. infantis* DSM20088, and *B. infantis* R0033.

The probiotic is present in the nutritional compositions in a total amount of at least about $10^3$ CFU/g, including from about $10^3$ CFU/g to about $10^{12}$ CFU/g, and including from about $10^6$ CFU/g to about $10^7$ CFU/g.

Macronutrients

As discussed above, in certain embodiments, the nutritional composition comprises one or more macronutrients selected from the group of protein, carbohydrate, fat, and mixtures thereof. In certain embodiments, the nutritional compositions comprise at least one source of protein, at least one source of carbohydrate, and at least one source of fat. Generally, any source of protein, carbohydrate, or fat that is suitable for use in nutritional products is also suitable for use herein, provided that such macronutrients are also compatible with the essential elements of the nutritional compositions as defined herein.

Although total concentration or amounts of protein, carbohydrates, and fat may vary depending upon the nutritional needs of the particular individual for whom the nutritional composition is formulated, such concentrations or amounts most typically fall within one of the following embodied ranges, inclusive of any other essential protein, carbohydrate, or fat ingredients as described herein.

Suitable ranges for proteins, carbohydrates, and fats in those embodiments where the nutritional composition is formulated as an infant formula or a pediatric formula, based on the percentage of total calories of the nutritional composition, are set forth in Table 1.

TABLE 1

| Macronutrient | Embodiment A (% Calories) | Embodiment B (% Calories) | Embodiment C (% Calories) |
|---|---|---|---|
| Protein | 2-75 | 5-50 | 7-40 |
| Carbohydrate | 1-85 | 30-75 | 35-65 |
| Fat | 5-70 | 20-60 | 25-50 |

Note:
Each numerical value in the table is preceded by the term "about."

Suitable ranges for proteins, carbohydrates, and fats in those embodiments where the nutritional composition is formulated as an adult nutritional product, based on the percentage of total calories of the nutritional composition, are set forth in Table 2.

TABLE 2

| Macronutrient | Embodiment D (% Calories) | Embodiment E (% Calories) | Embodiment F (% Calories) |
|---|---|---|---|
| Protein | 1-98 | 5-80 | 15-55 |
| Carbohydrate | 1-98 | 0-75 | 20-50 |
| Fat | 1-98 | 20-70 | 25-40 |

Note:
Each numerical value in the table is preceded by the term "about."

In certain embodiments, the nutritional composition includes protein or a source of protein. Generally, any source of protein may be used so long as it is suitable for oral nutritional compositions and is otherwise compatible with any other selected ingredients or features in the nutritional composition. Non-limiting examples of suitable proteins (and sources thereof) suitable for use in the nutritional compositions described herein include, but are not limited to, intact, hydrolyzed, or partially hydrolyzed protein, which may be derived from any known or otherwise suitable source such as milk (e.g., casein, whey), animal (e.g., meat, fish), cereal (e.g., rice, corn, wheat), vegetable (e.g., soy, pea, potato, bean), and combinations thereof. The protein may also include a mixture of amino acids (often described as free amino acids) known for use in nutritional products or a combination of such amino acids with the intact, hydrolyzed, or partially hydrolyzed proteins described herein. The amino acids may be naturally occurring or synthetic amino acids.

More particular examples of suitable protein (or sources thereof) used in the nutritional compositions disclosed herein include, but are not limited to, whole cow's milk, partially or completely defatted milk, milk protein concentrates, milk protein isolates, nonfat dry milk, condensed skim milk, whey protein concentrates, whey protein isolates, acid caseins, sodium caseinates, calcium caseinates, potassium caseinates, legume protein, soy protein concentrates, soy protein isolates, pea protein concentrates, pea protein isolates, collagen proteins, potato proteins, rice proteins, wheat proteins, canola proteins, *quinoa*, insect proteins, earthworm proteins, fungal (e.g., mushroom) proteins, hydrolyzed yeast, gelatin, bovine colostrum, human colostrum, glycomacropeptides, mycoproteins, proteins expressed by microorganisms (e.g., bacteria and algae), and combinations thereof. The nutritional compositions described herein may include any individual source of protein or combination of the various sources of protein listed above.

In addition, the proteins for use herein can also include, or be entirely or partially replaced by, free amino acids known for use in nutritional products, non-limiting examples of which include L-tryptophan, L-glutamine, L-tyrosine, L-methionine, L-cysteine, taurine, L-arginine, L-carnitine, and combinations thereof.

In certain embodiments, the nutritional compositions described herein include a protein component that consists of only intact or partially hydrolyzed protein; that is, the protein component is substantially free of any protein that has a degree of hydrolysis of 25% or more. In this context, the term "partially hydrolyzed protein" refers to proteins having a degree of hydrolysis of less than 25%, including less than 20%, including less than 15%, including less than 10%, and including proteins having a degree of hydrolysis of less than 5%. The degree of hydrolysis is the extent to which peptide bonds are broken by a hydrolysis chemical reaction. To quantify the partially hydrolyzed protein component of these embodiments, the degree of protein hydrolysis is determined by quantifying the amino nitrogen to total nitrogen ratio (AN/TN) of the protein component of the selected nutritional composition. The amino nitrogen component is quantified by USP titration methods for determining amino nitrogen content, while the total nitrogen component is determined by the Tecator® Kjeldahl method. These analytical methods are well known.

In certain embodiments, the nutritional composition includes a carbohydrate or a source of carbohydrate. The carbohydrate or source of carbohydrate suitable for use in the nutritional compositions disclosed herein may be simple, complex, or variations or combinations thereof. Generally, the carbohydrate may include any carbohydrate or carbohydrate source that is suitable for use in oral nutritional compositions and is otherwise compatible with any other selected ingredients or features in the nutritional composition. Non-limiting examples of carbohydrates suitable for use in the nutritional compositions described herein include, but are not limited to, maltodextrin; hydrolyzed or modified starch or cornstarch; polydextrose; glucose polymers; corn syrup; corn syrup solids; rice-derived carbohydrate; sucrose; glucose; fructose; lactose; high fructose corn syrup; honey; sugar alcohols (e.g., maltitol, erythritol, sorbitol); isomaltulose; sucromalt; pullulan; potato starch; and other slowly-digested carbohydrates; dietary fibers including, but not limited to, fructooligosaccharides (FOS), galactooligosaccharides (GOS), oat fiber, soy fiber, gum arabic, sodium carboxymethylcellulose, methylcellulose, guar gum, gellan gum, locust bean gum, konjac flour, hydroxypropyl methylcellulose, tragacanth gum, karaya gum, gum acacia, chitosan, arabinoglactins, glucomannan, xanthan gum, alginate, pectin, low methoxy pectin, high methoxy pectin, cereal beta-glucans (e.g., oat beta-glucan, barley beta-glucan), carrageenan and *psyllium*, digestion resistant maltodextrin (e.g., Fibersol™, a digestion-resistant maltodextrin, comprising soluble dietary fiber); soluble and insoluble fibers derived from fruits or vegetables; other resistant starches; and combinations thereof. The nutritional compositions described herein may include any individual source of carbohydrate or combination of the various sources of carbohydrate listed above.

In certain embodiments, the nutritional composition includes a fat or a source of fat. The fat or source of fat suitable for use in the nutritional compositions described herein may be derived from various sources including, but not limited to, plants, animals, and combinations thereof. Generally, the fat may include any fat or fat source that is suitable for use in oral nutritional compositions and is otherwise compatible with any other selected ingredients or features in the nutritional composition. Non-limiting examples of suitable fat (or sources thereof) for use in the nutritional compositions disclosed herein include coconut oil, fractionated coconut oil, soy oil, high oleic soy oil, corn oil, olive oil, safflower oil, high oleic safflower oil, medium chain triglyceride oil (MCT oil), high gamma linolenic (GLA) safflower oil, sunflower oil, high oleic sunflower oil, palm oil, palm kernel oil, palm olein, canola oil, high oleic canola oil, marine oils, fish oils, algal oils, borage oil, cottonseed oil, fungal oils, eicosapentaenoic acid (EPA), docosahexaenoic acid (DHA), arachidonic acid (ARA), conjugated linoleic acid (CLA), alpha-linolenic acid, rice bran oil, wheat bran oil, interesterified oils, transesterified oils, structured lipids, and combinations thereof. Generally, the fats used in nutritional compositions for formulating infant formulas and pediatric formulas provide fatty acids needed both as an energy source and for the healthy development of the infant, toddler, or child. These fats typically comprise triglycerides, although the fats may also comprise diglycerides, monoglycerides, and free fatty acids. Fatty acids provided by the fats in the nutritional composition include, but are not limited to, capric acid, lauric acid, myristic acid, palmitic acid, palmitoleic acid, stearic acid, oleic acid, linoleic acid, alpha-linolenic acid, ARA, EPA, and DHA. The nutritional compositions can include any individual source of fat or combination of the various sources of fat listed above.

Other Optional Ingredients

The nutritional compositions of the present disclosure may further comprise other optional components that may modify the physical, chemical, aesthetic or processing characteristics of the compositions or serve as pharmaceutical or additional nutritional components when used in the targeted population. Many such optional ingredients are known or otherwise suitable for use in medical food or other nutritional products or pharmaceutical dosage forms and may also be used in the compositions herein, provided that such optional ingredients are safe for oral administration and are compatible with the essential and other ingredients in the selected product form.

Non-limiting examples of such optional ingredients include preservatives, emulsifying agents, buffers, pharmaceutical actives, anti-inflammatory agents, additional nutrients as described herein, colorants, flavors, thickening agents and stabilizers, emulsifying agents, lubricants, and so forth.

The nutritional compositions may further comprise a sweetening agent, preferably including at least one sugar alcohol such as maltitol, erythritol, sorbitol, xylitol, mannitol, isolmalt, and lactitol, and also preferably including at least one artificial or high potency sweetener such as acesulfame K, aspartame, sucralose, saccharin, *stevia*, and tagatose. These sweetening agents, especially as a combination of a sugar alcohol and an artificial sweetener, are especially useful in formulating liquid beverage embodiments of the present disclosure having a desirable favor profile. These sweetener combinations are especially effective in masking undesirable flavors sometimes associated with the addition of vegetable proteins to a liquid beverage. Optional sugar alcohol concentrations in the nutritional composition may range from at least 0.01%, including from 0.1% to about 10%, and also including from about 1% to about 6%, by weight of the nutritional composition. Optional artificial sweetener concentrations may range from about 0.01%, including from about 0.05% to about 5%, also including from about 0.1% to about 1.0%, by weight of the nutritional composition.

A flowing agent or anti-caking agent may be included in the nutritional compositions as described herein to retard clumping or caking of the powder over time and to make a powder embodiment flow easily from its container. Any known flowing or anti-caking agents that are known or otherwise suitable for use in a nutritional powder or product form are suitable for use herein, non-limiting examples of which include tricalcium phosphate, silicates, and combinations thereof.

A stabilizer may also be included in the nutritional compositions. Any stabilizer that is known or otherwise suitable for use in a nutritional composition is also suitable for use herein, some non-limiting examples of which include gums such as xanthan gum. The stabilizer may represent from about 0.1% to about 5.0%, including from about 0.5% to about 3%, including from about 0.7% to about 1.5%, by weight of the nutritional composition.

Additionally, the nutritional compositions may comprise one or more antioxidants to provide nutritional support, as well as to reduce oxidative stress. Any antioxidants suitable for oral administration may be included for use in the nutritional compositions of the present disclosure, including, for example, vitamin A, vitamin C, and retinol, as well as tocopherols and carotenoids (e.g., zeaxanthin, lycopene, and beta-carotene) other than those mentioned above.

The nutritional compositions may further comprise any of a variety of other vitamins or related nutrients, non-limiting examples of which include vitamin D, vitamin K, thiamine, riboflavin, pyridoxine, vitamin B12, niacin, folic acid, pantothenic acid, biotin, choline, inositol, salts and derivatives thereof, and combinations thereof.

The nutritional compositions may further comprise any of a variety of other additional minerals, non-limiting examples of which include calcium, phosphorus, magnesium, iron, zinc, manganese, copper, sodium, potassium, molybdenum, chromium, chloride, and combinations thereof.

The nutritional compositions may additionally comprise nucleotides and/or nucleotide precursors selected from the group consisting of nucleoside, purine base, pyrimidine base, ribose and deoxyribose to further improve intestinal barrier integrity and/or maturation. The nucleotide may be in monophosphate, diphosphate, or triphosphate form. The nucleotide may be a ribonucleotide or a deoxyribonucleotide. The nucleotides may be monomeric, dimeric, or polymeric (including RNA and DNA). The nucleotide may be present in the nutritional composition as a free acid or in the form of a salt, preferably a monosodium salt.

Suitable nucleotides and/or nucleosides for use in the nutritional compositions include one or more of cytidine 5'-monophosphate, uridine 5'-monophosphate, adenosine 5'-monophosphate, guanosine 5'-1-monophosphate, and/or inosine 5'-monophosphate, more preferably cytidine 5'-monophosphate, uridine 5'-monophosphate, adenosine 5'-monophosphate, guanosine 5'-monophosphate, and inosine 5'-monophosphate.

Methods of Manufacture

The nutritional compositions of the present disclosure may be prepared by any known or otherwise effective manufacturing technique for preparing the selected product solid or liquid form. Many such techniques are known for any given product form such as nutritional liquids or powders and can easily be applied by one of ordinary skill in the art to the nutritional compositions described herein.

The nutritional compositions of the present disclosure can therefore be prepared by any of a variety of known or otherwise effective formulation or manufacturing methods.

In one suitable manufacturing process, for example, at least three separate slurries are prepared, including a protein-in-fat (PIF) slurry, a carbohydrate-mineral (CHO-MN) slurry, and a protein-in-water (PIW) slurry. The PIF slurry is formed by heating and mixing the oil (e.g., canola oil, corn oil, etc.) and then adding an emulsifier (e.g., lecithin), fat soluble vitamins, and a portion of the total protein (e.g., milk protein concentrate, etc.) with continued heat and agitation. The CHO-MIN slurry is formed by adding with heated agitation to water: minerals (e.g., potassium citrate, dipotassium phosphate, sodium citrate, etc.), trace and ultra trace minerals (TM/UTM premix), thickening or suspending agents (e.g. avicel, gellan, carrageenan). The resulting CHO-MIN slurry is held for 10 minutes with continued heat and agitation before adding additional minerals (e.g., potassium chloride, magnesium carbonate, potassium iodide, etc.), and/or carbohydrates (e.g., HMOs, fructooligosaccharide, sucrose, corn syrup, etc.). The PIW slurry is then formed by mixing with heat and agitation the remaining protein, if any.

The resulting slurries are then blended together with heated agitation and the pH adjusted to 6.6-7.0, after which the composition is subjected to high-temperature short-time (HTST) processing during which the composition is heat treated, emulsified and homogenized, and then allowed to cool. Water soluble vitamins and ascorbic acid are added, the pH is adjusted to the desired range if necessary, flavors are added, and water is added to achieve the desired total solid level. The composition is then aseptically packaged to form an aseptically packaged nutritional liquid (e.g., emulsion). This nutritional liquid can then be further diluted, heat-treated, and packaged to form a ready-to-feed or concentrated liquid, or it can be heat-treated and subsequently processed and packaged as a reconstitutable powder, e.g., spray dried, drymixed, agglomerated.

When in the form of a nutritional solid, such as a spray dried nutritional powder or drymixed nutritional powder, the nutritional composition may be prepared by any collection of known or otherwise effective techniques, suitable for making and formulating a nutritional powder.

For example, when the nutritional powder is a spray dried nutritional powder, the spray drying step may likewise include any spray drying technique that is known for or otherwise suitable for use in the production of nutritional powders. Many different spray drying methods and techniques are known for use in the nutrition field, all of which are suitable for use in the manufacture of the spray dried nutritional powders herein.

One method of preparing the spray dried nutritional powder comprises forming and homogenizing an aqueous slurry or liquid comprising predigested fat, and optionally protein, carbohydrate, and other sources of fat, and then spray drying the slurry or liquid to produce a spray dried nutritional powder. The method may further comprise the step of spray drying, drymixing, or otherwise adding additional nutritional ingredients, including any one or more of the ingredients described herein, to the spray dried nutritional powder.

Methods of Use

The nutritional compositions described herein can be used to address one or more of the diseases, disorders, or conditions discussed herein, or can be used to provide one or more of the benefits described herein, to preterm infants, infants, toddlers, children, and adults. The preterm infant, infant, toddler, child, or adult utilizing the nutritional compositions described herein may actually have or be afflicted with the disease or condition described, or may be susceptible to, or at risk of, getting the disease or condition (that is, may not actually yet have the disease or condition, but is at elevated risk as compared to the general population for getting it due to certain conditions, family history, etc.) Whether the preterm infant, infant, toddler, child, or adult actually have the disease or condition, or is at risk or susceptible to the disease or condition, the preterm infant, infant, toddler, child, or adult are classified herein as "in need of" assistance in dealing with and combating the disease or condition. For example, the bottle-fed infant (also referred to as a formula-fed infant), preterm infant, infant, toddler, child, or adult may actually have gut dysbiosis (or simply "dysbiosis") or may be at risk of getting gut dysbiosis (i.e., susceptible to getting dysbiosis) due to family history or other medical conditions, for example. Whether the bottle-fed infant, preterm infant, infant, toddler, child, or adult actually has the disease or condition, or is only at risk or susceptible to getting the disease or condition, it is within the scope of the present disclosure to assist the bottle-fed infant, preterm infant, infant, toddler, child, or adult with the nutritional compositions described herein.

In certain embodiments, the nutritional compositions described herein provide a synergistic benefit to the consumer promoting the colonization of beneficial intestinal microbiota in order to discourage the growth of harmful bacteria, thereby improving the balance of beneficial microflora in the gastrointestinal tract. While not wishing to be bound by theory, Applicants believe that by promoting the growth of beneficial bacteria harmful (or at least other than beneficial bacteria) are effectively out competed, leaving the individual with an overall healthier population of bacteria.

Based on the foregoing, because some of the method embodiments of the present disclosure are directed to specific subsets or subclasses of identified individuals (that is, the subset or subclass of individuals "in need of" assistance in addressing one or more specific diseases or specific conditions noted herein), not all preterm infants, infants, toddlers, children, and adults will fall within the subset or subclass of preterm infants, infants, toddlers, children, and adults, as described herein for certain diseases or conditions. Non-limiting examples of individuals that may be considered "in need of" assistance in addressing one or more specific diseases or specific conditions noted herein, include bottle-fed infants, infants born by cesarean section, individuals on antibiotic therapy, preterm infants, and individuals (e.g., preterm infants, infants, toddlers, children, and adults) who have or have had a gastrointestinal infection.

The nutritional compositions as described herein comprise 2'-fucosyllactose, lutein, and RRR-alpha-tocopherol and are used to improve at least one of gut function, gut health, and gut development. For example, the nutritional compositions disclosed herein control, treat, and reduce a number of diseases, disorders and conditions related to the gastrointestinal tract, especially those related to gut maturation and proper microbiotic profile/balance in the gastrointestinal tract (e.g. dysbiosis). Specifically, the nutritional compositions of the present disclosure promote the growth of beneficial bacteria, thereby promoting a healthy balance of gut flora. Administration of the nutritional compositions of the present disclosure improve intestinal/gut barrier integrity. Administration of the nutritional compositions of the present disclosure improve feeding tolerance (e.g., reduced diarrhea, loose stools, gas, and bloating), otherwise referred to as treating feeding intolerance. Administration of the nutritional compositions of the present disclosure reduce (treat) colic in infants. Administration of the nutritional compositions of the present disclosure protect against necrotizing enterocolitis and other disorders of prematurity. Administration of the nutritional compositions of the present disclosure treat gastrointestinal diseases and disorders associated with the enteric nervous system. Administration of the nutritional compositions of the present disclosure treat gastrointestinal diseases and disorders of gut contractility and inflammation. Administration of the nutritional compositions of the present disclosure correct effects of gut dysbiosis. Administration of the nutritional compositions of the present disclosure affect long-term modulation of allergic tolerance (e.g., treat and/or reduce the symptoms of food allergy).

In certain embodiments, the nutritional compositions are administered to an individual having, susceptible to, or at risk of, gastrointestinal diseases and disorders associated with gut dysbiosis. In certain embodiments, the nutritional compositions are administered to an individual having, susceptible to, or at risk of, gastrointestinal diseases and disorders associated with dysbiosis and/or inflammation. Diseases which fall within these categories include, but are not limited to, irritable bowel syndrome, colitis (e.g., necrotizing enterocolitis, Crohn's disease, ischemic colitis, *cryptosporidium* enterocolitis, pseudomembranous colitis, cytomegalovirus, ulcerative colitis), irritable bowel disease, celiac disease, obesity, metabolic syndrome, food intolerance, and food allergies.

In certain embodiments, the nutritional compositions are administered to an individual that is otherwise considered a healthy individual. That is, the individual is not considered "in need" of a nutritional intervention to treat conditions and diseases such as those described above. Thus, certain embodiments contemplate use of the nutritional compositions for improvement in gut health or gut development in a healthy individual. In addition, certain embodiments contemplate non-therapeutic use of the nutritional compositions for promoting gut health and/or gut development.

Along with improved growth of beneficial microbiota as described above, the use of the nutritional compositions of the present disclosure also function to enhance the individual's ability to resist microbial infection. The use of the nutritional compositions of the present disclosure also promote growth and maturation of an individual's immune system in the gastrointestinal tract of an infant, toddler, child, or adult.

EXAMPLES

The following examples illustrate specific embodiments and/or features of the nutritional compositions and methods of the present disclosure. The examples are given solely for the purpose of illustration and are not to be construed as limitations of the present disclosure, as many variations thereof are possible without departing from the spirit and scope of the disclosure. All exemplified amounts are weight percentages based upon the total weight of the composition, unless otherwise specified.

The exemplified compositions are shelf stable nutritional compositions prepared in accordance with the manufacturing methods described herein, such that each exemplified composition, unless otherwise specified, includes an aseptically processed embodiment and a retort packaged embodiment.

Example 1: The following example illustrates a ready-to-feed nutritional emulsion according to the general inventive concepts, the ingredients of which are listed in the table below. All ingredient amounts are listed as kilogram per 1000 kilogram batch of product, unless otherwise specified (Table 3).

TABLE 3

| INGREDIENTS | APPROXIMATE AMOUNT PER 1000 KG |
| --- | --- |
| Skim milk | 2059.0 kg |
| Lactose | 413.4 kg |
| High oleic sunflower oil | 111.1 kg |
| Whey protein concentrate | 87.2 kg |
| Soy oil | 83.4 kg |
| Coconut oil | 75.8 kg |
| Fructooligosaccharide (FOS) | 20.8 kg |
| Whey protein | 5.6 kg |
| Potassium citrate | 3.4 kg |
| Arachidonic acid (AA) | 2.9 kg |
| Nucleotide/choline premix | 2.3 kg |
| Choline bitartrate | 1.2 kg |
| Cytidine 5'-monophosphate | 241.7 g |
| Disodium guanosine 5'-monophosphate | 175.9 g |
| Disodium uridine 5'-monophosphate | 153.1 g |
| Adenosine 5'-monophosphate | 91.9 g |
| Maltodextrin (premix diluent) | q.s. |
| 2'-Fucosyllactose (2'-FL) | 1.84 kg |
| Lecithin, PCR negative, IP | 1.72 kg |
| Calcium carbonate | 1.61 kg |
| Docosahexaenoic acid (DHA) | 1.52 kg |
| Ascorbic acid | 1.51 kg |
| Vitamin trace mineral premix | 1.13 kg |
| Taurine | 401.7 g |
| myo-Inositol | 243.3 g |
| Ferrous sulfate | 122.6 g |
| Zinc sulfate | 97.8 g |
| Niacinamide | 55.0 g |
| Calcium d-pantothenate | 39.6 g |
| Copper sulfate | 10.7 g |
| Thiamin HCl | 8.1 g |
| Pyridoxine HCl | 4.6 g |
| Riboflavin | 4.3 g |
| Manganese sulfate | 3.0 g |
| Folic acid | 746.7 mg |
| Biotin | 222.9 mg |
| Sodium selenate | 110.2 mg |
| Cyanocobalamin | 7.1 mg |
| Dextrose anhydrous (premix diluent) | q.s. |
| Magnesium chloride | 704.1 g |
| Mixed carotenoid premix | 650.2 g |
| Lutein | 1.3 g |
| β-carotene | 715.2 mg |
| High oleic safflower oil (premix diluent) | q.s. |
| Potassium hydroxide | 609.4 g |
| Vitamin A, D$_3$, E, K$_1$ premix | 334.5 g |
| Vitamin E (d-α-tocopheryl acetate) | 113.2 g |
| Vitamin A (retinyl palmitate) | 12.5 g |
| Vitamin K$_1$ (phylloquinone) | 587.1 mg |
| Vitamin D$_3$ (cholecalciferol) | 88.3 mg |
| Coconut or sunflower oil (premix diluent) | q.s. |
| L-tryptophan | 277.0 g |
| Ascorbyl palmitate | 200.6 g |
| Sodium chloride | 200.0 g |
| Tocopherol-2 | 107.0 g |
| Mixed tocopherols | 77.6 g |
| Sunflower oil (diluent) | q.s. |
| Ferrous sulfate | 99.8 g |
| L-carnitine | 26.5 g |
| Calcium chloride | 10 g |
| Tricalcium phosphate | 10 g |
| Potassium iodide | 526.2 mg |
| Citric acid | As needed |
| Ingredient water | As needed |

Example 2: A series of experiments were carried out to determine the effects of providing 2'-FL, lutein, and RRR-alpha-tocopherol on bacterial growth. Fecal fermentations were carried out by using 3 ml fermentations in 10 ml fermentor (24 multi-well plate; μ-24 Bioreactor, Applikon Biotechnology). Fresh faecal sample came from a formula (without prebiotic or probiotic)-fed baby. Stools were vacuum stored in refrigerated conditions until the fermentation. Fresh feces were weighed and dissolved in Mc Bain and MacFarlane medium (1:5) to hydrate them. Three milliliters of the homogenized mixture (faecal slurry) were inoculated in each fermenter. In each case, prebiotic (2'-FL), RRR-alpha-tocopherol (vitamin E) and lutein were added at different dosage (Table 4). Before starting fermentation, headspace was removed with the aim of nitrogen. All the protocol procedures were performed in anaerobic conditions. Anaerobiosis, temperature (37° C.) and pH levels (pH 5.5) were maintained during the assay and monitored throughout the study.

TABLE 4

| Conditions | 2'-FL (1 g) DD | Lutein (132 μg) DD | RRR-alpha-tocopherol (10.3 mg) DD |
| --- | --- | --- | --- |
| Control 0 h | — | — | — |
| Control 24 h | — | — | — |
| 2'-FL DD | X | — | — |
| Blend + 2'-FL DD | X | X | X |
| Blend DD | — | X | X |

| | 2'-FL (200 mg) DI | Lutein (24.4 μg) DI | RRR-alpha-tocopherol (2.06 mg) DI |
| --- | --- | --- | --- |
| 2'-FL DI | X | | |
| Blend + 2'-FL DI | X | X | X |
| Blend DI | | X | X |

| | 2'-FL (200 mg) DI | Lutein (132 μg) DD | RRR-alpha-tocopherol (10.3 mg) DD |
| --- | --- | --- | --- |
| Blend(DD) + 2'-FL(DI) | X | X | X |

DI, dose per intake (dose equivalent to one serving of an infant formula); DD, daily dose; (assuming five intakes per day); Blend: Lutein + RRR-alpha-tocopherol;

Once obtained, slurry samples were immediately frozen and stored at −20° C. until their processing. DNA from samples was isolated following Yuang and co-workers with minor modifications, with the aid of MagnaPure Compact System (Roche Life Science), to avoid bias in DNA purification toward misrepresentation of gram positive bacteria. For large scale sequencing, the hypervariable region V3-V4 of the bacterial 16s rRNA gene was amplified using key-tagged eubacterial primers10 and sequenced with a MiSeq Illumina Platform, following the Illumina recommendations for Library preparation and sequencing for metagenomics studies.

The resulting sequences were split taking into account the barcode introduced during the PCR reaction. Quality control of the sequences was performed in different steps, i) quality filtering (with a minimum threshold of Q20) was performed using fastx tool kit version 0.013, ii) primer (16s rRNA primers) trimming and length selection (reads over 300 nts) was done with cutadapt version 1.2. These FASTQ files were converted to FASTA files and UCHIME program version 7.0.1001 was used in order to remove chimeras that could arise during the amplification and sequencing step. Those clean FASTA files were BLAST against NCBI 16s rRNA database using blastn version 2.2.29+. The resulting XML files were processed using a pipeline developed internally in order to annotate each sequence at different phylogenetic levels (Phylum, Family, Genus and Species). Alpha diversity was conducted using specaccum program in the vegan package as implemented for R version 3.1.1. Presence results (as percentage of each group sequences) are expressed as the mean and standard deviation. Results were compared among the different assays using Tukey's multiple comparison tests.

For quantification, previous extracted DNA was used. Real-time PCR was used to quantify genera *Bifidobacterium* and *Lactobacillus*, and *B. longum* and *L. fermentum* species. In the case of genus *Bifidobacterium* and *B. longum*, quantification was performed with primers described by Matsuki et al.1. *Lactobacillus* group was quantified with primers described by Byun et al.2. *Lactobacillus fermentum* was quantified with the aid of primers designed by Matsuda et al.3 Nucleotide sequences of primers are listed in Table 5. Oligonucleotides were purchased from Thermo Fischer (Thermo Fisher Scientific).

TABLE 5

| Target | Primer | Sequence (5'-3') |
|---|---|---|
| Genus Bifidobacterium | g-BIFID-F | CTCCTGGAAACGGGTGG |
|  | g-BIFID-R | GGTGTTCTTCCCGATATCTACA |
| Genus Lactobacillus | LACTOF | TGGAAACAGRTGCTAATACCG |
|  | LACTOR | GTCCATTGTGGAAGATTCCC |
| B. longum | BiLON-1 | TTCCAGTTGATCGCATGGTC |
|  | BiLON-2 | GGGAAGCCGTATCTCTACGA |
| L. fermentum | LFer-1 | CCTGATTGATTTTGGTCGCCAAC |
|  | LFer-2 | ACGTATGAACAGTTACTCTCATACGT |

In all cases, PCRs were performed with the aid of SYBR® Green PCR Master Mix (Applied Biosystems). Thermal cycling conditions were: 50° C. for 2 min, 95° C. for 10 min for AmpliTaq Gold enzyme activation, and 40 cycles of 95° C. for 15 sec and extension at 60° C. for 1 min. In all cases, PCR was performed in triplicate in a StepOne Real-Time PCR System (Applied Biosystems). Data analysis was performed using StepOne software. In all cases, standard curve was constructed with DNA coming from 10-fold diluted standardized cultures.

DNA samples isolated from fecal slurries were analyzed for *Bifidobacterium* spp., *Lactobacillus* spp., *Bifidobacterium longum* and *Lactobacillus fermentum* quantification. In total, 27 samples for each taxonomical group.

Quantification of genus *Bifidobacterium* by real-time PCR is shown in FIG. 1. Addition of 2'-FL at both daily and per intake doses rendered significant higher bifidobacteria numbers (p-value <0.05, comparison between 2'-FL (DD) and blend (DD); p-value <0.05, comparison between 2'-FL (DI) and blend (DI)). The combination of 2'-FL (per intake) and blend (RRR-alpha-tocopherol+lutein; daily) obtained the highest bifidobacteria quantification (p-value <0.05 compared with 2'-FL (DD); p-value <0.001 compared with control 24 h). As can be seen from the figure, the combination of 2'-FL, lutein, and RRR-alpha-tocopherol provide a synergistic benefit to the growth of beneficial bacteria. Specifically, the Bifidobacteria grows at a rate that would not otherwise be expected from administration of the individual components.

Figure 2:
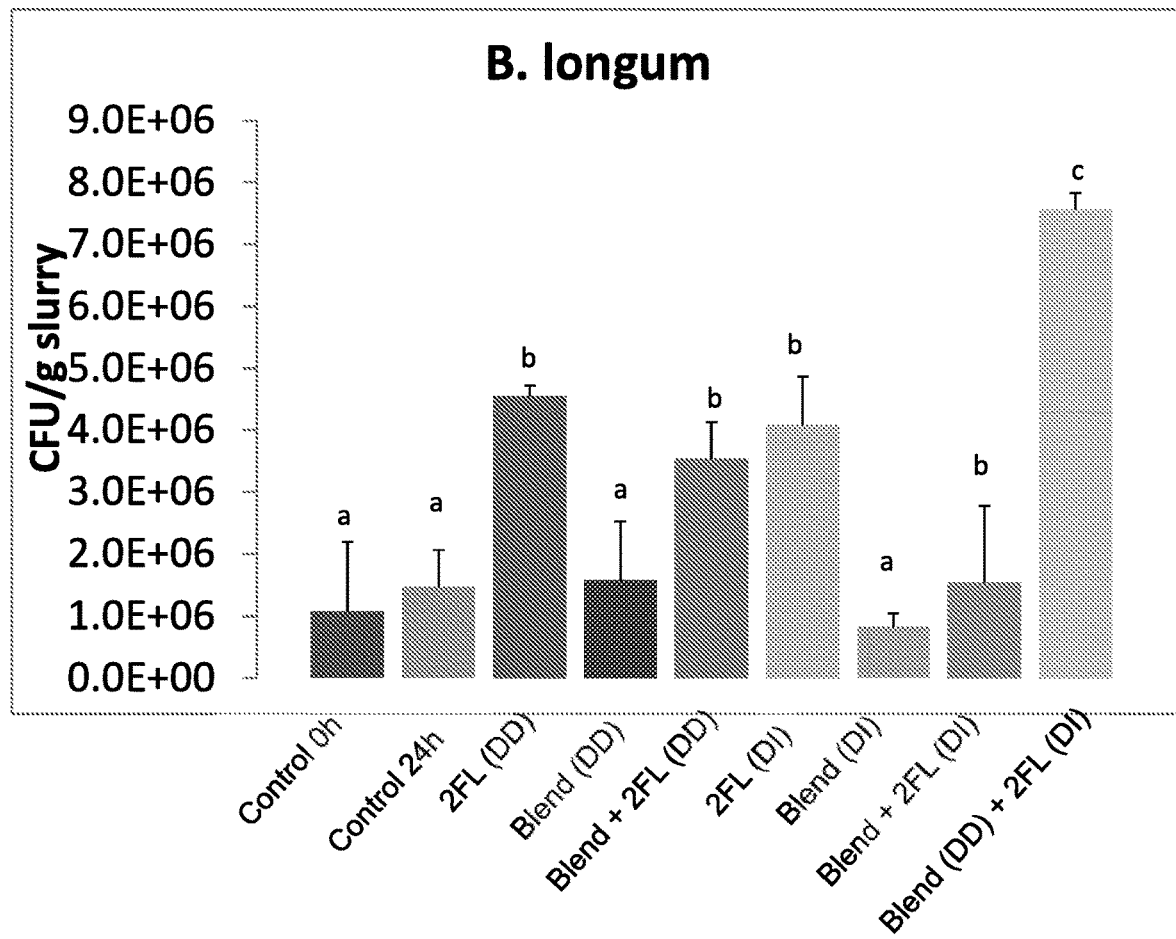
FIG. 2 is a graph showing the concentration of *B. longum* in fecal samples after exposure to a variety of mixtures, measured by real time-PCR. Bars with different letters are significantly different at $p<0.05$.

Quantification of *B. longum* species by real-time PCR is shown in FIG. 2. As in the case of genus *Bifidobacterium*, the addition of 2'-FL at both daily and per intake doses rendered significant higher *B. longum* numbers (p-value <0.05, comparison between 2'-FL (DD) and product (DD); p-value <0.05, comparison between 2'-FL (DI) and blend (DI)). The combination of 2'-FL (per intake) and blend (RRR-alpha-tocopherol+lutein; daily) obtained the highest bifidobacteria quantification (p-value <0.05 compared with 2'-FL (DD); p-value <0.001 compared with control 24 h).

Figure 3:
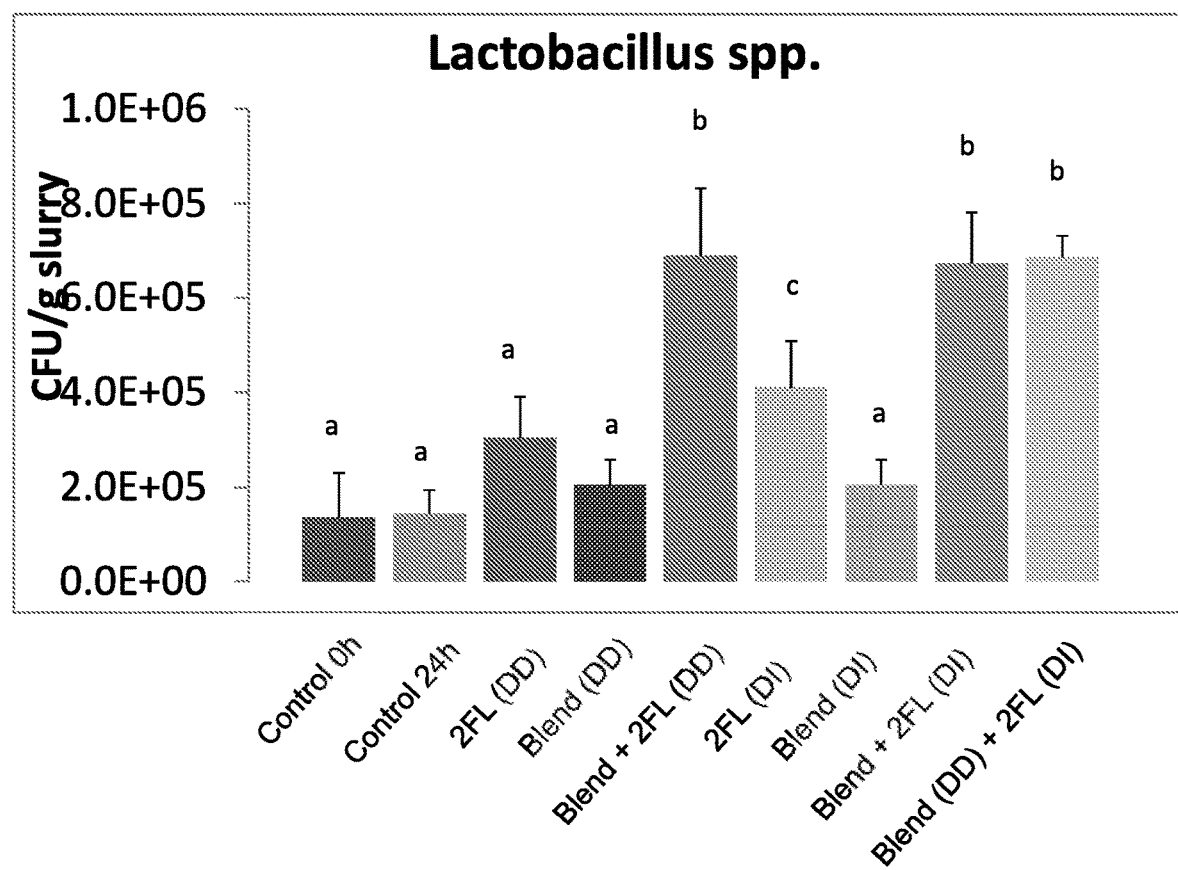
FIG. 3 is a graph showing the concentration of Lactobacilli in fecal samples after exposure to a variety of mixtures, measured by real time-PCR. Bars with different letters are significantly different at $p<0.05$.

Quantification of genus *Lactobacillus* by real-time PCR is shown in FIG. 3. In all cases, the combination of 2'-FL and product (vitamin E+lutein) obtained the highest Lactobacilli quantification. The addition of 2'-FL together with the product rendered significant higher Lactobacilli numbers than just with the addition of 2'-FL or the product (p-value <0.001, comparison between 2'-FL (DD) and 2'-FL+product (DD); p-value <0.05, comparison between 2'-FL (DI) and 2'-FL+product (DI)). As can be seen from the figure, the combination of 2'-FL, lutein, and RRR-alpha-tocopherol provide a synergistic benefit to the growth of beneficial bacteria. Specifically, the *Lactobacillus* grows at a rate that would not otherwise be expected from administration of the individual components.

Figure 4:
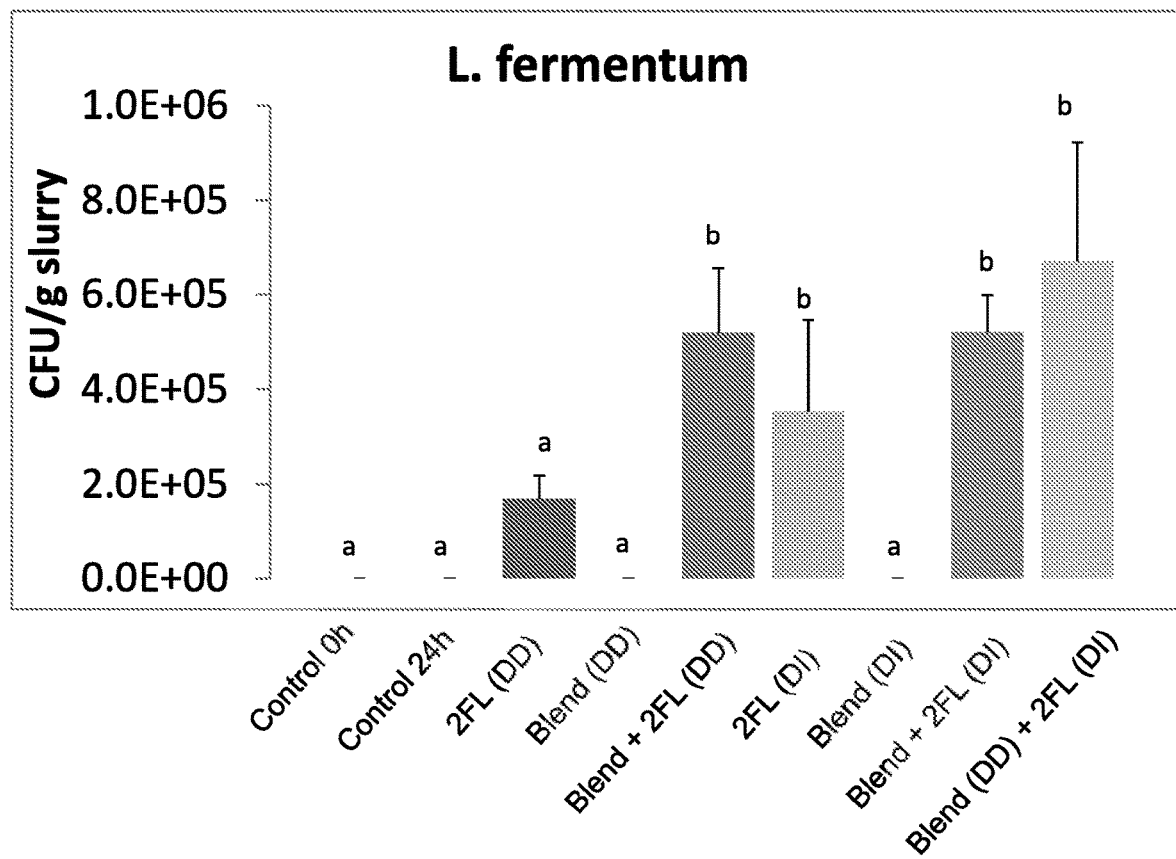
FIG. 4 is a graph showing the concentration of *L. fermentum* in fecal samples after exposure to a variety of mixtures, measured by real time-PCR. Bars with different letters are significantly different at $p<0.05$.

Quantification of *L. fermentum* species by real-time PCR is shown in FIG. 4. No detection was obtained in samples coming from both controls (0 h and 24 h), and with blend (RRR-alpha-tocopherol+lutein) added alone (detection limit 1.00·10³ CFU/g slurry). The addition of 2'-FL reached detectable values, being the highest but not significantly different value the combination of 2'-FL (per intake) and blend (RRR-alpha-tocopherol+lutein; daily). In both, dosage per intake and daily dose, results were higher (not significant) in the case of the combination of 2'-FL and product.

The synergistic growth profiles demonstrated by the examples provides benefits to one or more of the diseases and conditions discussed herein, including but not limited to gut health, gut function, and gut maturation. The enhanced growth promotes a healthy balance of beneficial bacteria in the gastrointestinal tract (e.g., treat gut dysbiosis) thereby treating and/or preventing gastrointestinal diseases and/or disorders resulting from suboptimal gastrointestinal flora population/balance.

In certain embodiments, it may be possible to utilize the various inventive concepts in combination with one another (e.g., one or more of the first, second, third, etc., exemplary embodiments may be utilized in combination with each other). Additionally, any particular element recited as relating to a particularly disclosed embodiment should be interpreted as available for use with all disclosed embodiments, unless incorporation of the particular element would be contradictory to the express terms of the embodiment. Additional advantages and modifications will be readily apparent to those skilled in the art. Therefore, the disclosure, in its broader aspects, is not limited to the specific details presented therein, the representative apparatus, or the illustrative examples shown and described. Accordingly, departures may be made from such details without departing from the spirit or scope of the general inventive concepts.

The invention claimed is:

1. A method of improving the gut health of an infant, the method comprising administering an amount of a nutritional composition comprising therapeutically effective amounts of the human milk oligosaccharide 2'-fucosyllactose, lutein, and RRR-alpha-tocopherol to the infant.

2. The method of claim 1, wherein administration increases beneficial bacteria in the gut of the infant.

3. The method of claim 1, wherein the nutritional composition comprises 2'-fucosyllactose in an amount of about 0.02 mg/mL to about 20 mg/mL.

4. The method of claim 1, wherein the nutritional composition comprises lutein in an amount of about 0.001 mg/mL to about 5 mg/mL.

5. The method of claim 1, wherein the nutritional composition comprises RRR-alpha-tocopherol in an amount of about 3 mg/L to about 100 mg/L.

6. The method of claim 1, wherein the nutritional composition is an infant formula.

7. The method of claim 1, wherein the nutritional composition further comprises a probiotic.

8. The method of claim 1, wherein the probiotic is a *Bifidobacterium*.

9. The method of claim 1, wherein the nutritional composition further comprises a second human milk oligosaccharide.

10. A method of increasing the beneficial bacteria in the gastrointestinal tract of an infant in need thereof, the method comprising administering an amount of a nutritional composition comprising therapeutically effective amounts of the human milk oligosaccharide 2'-fucosyllactose, lutein, and RRR-alpha-tocopherol to the infant.

11. The method of claim 10, wherein the beneficial bacteria is at least one of a *Bifidobacterium* and a *Lactobacillus*.

12. The method of claim 10, wherein the nutritional composition comprises 2'-fucosyllactose in an amount of about 0.02 mg/mL to about 20 mg/mL.

13. The method of claim 10, wherein the nutritional composition comprises lutein in an amount of about 0.001 mg/mL to about 5 mg/mL.

14. The method of any claim 10, wherein the nutritional composition comprises RRR-alpha-tocopherol in an amount of about 3 mg/L to about 100 mg/L.

15. The method claim 10, wherein the nutritional composition is an infant formula.

16. The method claim 10, wherein the nutritional composition further comprises a probiotic.

17. The method of claim 10, wherein the nutritional composition further comprises a second human milk oligosaccharide.

* * * * *

UNITED STATES PATENT AND TRADEMARK OFFICE
CERTIFICATE OF CORRECTION

PATENT NO. : 11,260,088 B2
APPLICATION NO. : 16/625429
DATED : March 1, 2022
INVENTOR(S) : Alejandro Barranco Perez et al.

Page 1 of 1

It is certified that error appears in the above-identified patent and that said Letters Patent is hereby corrected as shown below:

On the Title Page

Item (12) "Barranco" should read -- Perez et al. --.

Item (72) Inventor 1 was listed as Alejandro Perez BARRANCO.
The correct name for Inventor 1 should be Alejandro Barranco PEREZ.

Signed and Sealed this
Sixteenth Day of April, 2024

Katherine Kelly Vidal
*Director of the United States Patent and Trademark Office*